United States Patent
See

(10) Patent No.: US 6,884,420 B2
(45) Date of Patent: Apr. 26, 2005

(54) COMPOSITION AND METHOD FOR REDUCING BLOOD GLUCOSE

(75) Inventor: Darryl See, Laguna Niguel, CA (US)

(73) Assignee: Cross Bay, LLC, Las Vegas, NV (US)

( * ) Notice: Subject to any disclaimer, the term of this patent is extended or adjusted under 35 U.S.C. 154(b) by 54 days.

(21) Appl. No.: 10/440,110

(22) Filed: May 19, 2003

(65) Prior Publication Data

US 2004/0234513 A1 Nov. 25, 2004

(51) Int. Cl.⁷ .................... A61K 35/84; A61K 35/78
(52) U.S. Cl. .................... 424/195.15; 424/725
(58) Field of Search .................. 424/195.15, 725, 424/641, 702, 655, 617; 514/54

(56) References Cited

U.S. PATENT DOCUMENTS

| 5,847,109 | A | * | 12/1998 | Garti et al. | 536/123 |
| 6,589,566 | B1 | * | 7/2003 | Ueda et al. | 424/617 |
| 2002/0044942 | A1 | * | 4/2002 | Dopson | 424/184.1 |
| 2003/0181401 | A1 | * | 9/2003 | Takada et al. | 514/42 |

* cited by examiner

*Primary Examiner*—Christopher R. Tate
(74) *Attorney, Agent, or Firm*—Dennison, Schultz, Dougherty & MacDonald

(57) ABSTRACT

A composition for reducing blood sugar in humans in need thereof, contains *Agaricus blazeii*, alpha lipoic acid, transfer factor, polymannose, fenugreek, coenzyme Q-10, selenium, zinc, vitamin C, vitamin E, chromium and vanadium.

7 Claims, No Drawings

COMPOSITION AND METHOD FOR REDUCING BLOOD GLUCOSE

BACKGROUND OF THE INVENTION

The invention relates to the field of compositions for treatment of diabetes, either type II (non-insulin dependent diabetes) or type I (juvenile-onset) diabetes.

Diabetes Mellitus (DM) is the most common chronic degenerative disease in the world. In the US alone, it is the third leading cause of disease, accounts for over 10% of all hospitalizations and costs our health care system over 20 billion dollars per year. Some populations, such as Hispanics, Native Americans and the southern Africans, have a prevalence of over 30%. Despite advances in treatment, complications such as heart disease, renal failure, glaucoma, blindness, chronic ulcers, painful neuropathy, Charcot's joints and amputations will occur at a high rate as a result of chronically elevated serum blood glucose levels.

There are two forms of diabetes, Type I and Type II. Type I, or insulin-requiring, is characterized by autoimmune destruction of the insulin-producing islet cells in the pancreas. Molecular mimicry with certain viruses such as coxsackieviruses and other antigens such as those found in milk may be the cause. Glutamate decarboxylase on the target islet cell may be the binding site for the cross-reacting immune cells. Lack of insulin leads to an excess of glucose in the blood and resultant complications such as heart and kidney disease.

Type II DM is characterized by cellular resistance to insulin, once again resulting in high blood glucose levels. The mechanism of Type II DM is multifactorial. Thus, immunological abnormalities have been found, viruses have been implicated, target cells have insulin resistance, weight is an important factor, the pancreas underproduces insulin, and high blood sugar causes cellular dysfunction in many organ systems. Furthermore, complications lead to considerable mortality and morbidity.

The therapy for Type I DM is insulin replacement, but either too high or too low of a dose can lead to disastrous complications like diabetic coma and heart attacks. Administration of insulin also accelerates the aging process in cells and tissues, it speeds up plaque production on coronary arteries, it can actually raise blood sugar levels, it can block DNA, RNA, protein and glucose synthesis and it can result in central nervous system and circulatory depression, even leading to death. Oral hypoglycemic agents can cause nausea, diarrhea, fatigue, excess insulin levels, suppressed cellular function, headaches, muscle aches, decreased concentration and rashes.

Type II DM can be treated with drugs that lower cellular resistance to insulin and stimulate its release, but this approach may also lead to toxicity from the medications.

A natural approach to DM would seem logical given the complications and shortcomings of treatment with drugs and insulin. The normal body homeostasis and feedback mechanisms can be maintained to restore normal blood glucose and insulin levels; side effects are eliminated. The cost to society may be lowered by reducing cost of treatment of both the disease and also complications may be decreased.

SUMMARY OF THE INVENTION

It is therefore an object of the invention to provide a composition that addresses the underlying mechanisms of diabetes mellitus.

To achieve this and other objects, the invention is directed to a combination of herbs, minerals and natural components of the body, which reduces blood sugar to lower levels on a consistent basis and may prevent the mortality and morbidity of this disease, while being non-toxic and without side effects. Thus, the components of the invention were selected to lower blood sugar levels, insulin requirements and complications of diabetes without toxicity.

DETAILED DESCRIPTION OF THE INVENTION

The preferred composition of the invention contains, in percent by weight, the following components in approximate amounts:

| | |
|---|---|
| *Agaricus blazeii* | 20–30 |
| alpha lipoic acid | 15–20 |
| transfer factor | 15–20 |
| polymannose | 20–30 |
| fenugreek | 4–6 |
| coenzyme Q-10 | 8–12 |
| selenium | 0.01–0.03 |
| zinc | 0.1–0.3 |
| vitamin C | 4–6 |
| vitamin E | 3–5 |
| chromium | 0.004–0.01 |
| vanadium | 0.001–0.004 |

*Agaricus blazeii* is a mushroom found in South America, Japan and Korea. Various mushrooms of the Agaricaceae family are known to have insulin potentiating activity, as disclosed for example in U.S. Pat. No. 6,200,569 to Cheng. The extract of this mushroom appears to regulate the immune system, resulting in decreased immune-mediated damage from high glucose levels and also improving resistance to infection.

Alpha-lipoic acid is a potent antioxidant is found in all cells in small amounts, and is decreased in diabets patients. Oxidative stress is responsible for many of the complications of diabetes and this cellular component may decrease them. Moreover, as discussed in U.S. Pat. No. 5,948,810 to Wessel et al, it has been reported in the literature that R,S-(+,-)-alpha-lipoic acid has a blood sugar-lowering effect in the case of alloxan-induced diabetes in the animal model. In this connection, it has not been resolved whether this effect due to interference with the secretion of insulin or directly due to the activation of the pyruvate dehydrogenase (C. V. Natraj et al., J. Biosci. vol. 6(1), 37–46 (1984)). Metabolic deviations resulting from diabetes, such as hyperglycemia, ketonemia, ketonuria, reduced glycogen in the tissue and a decreased synthesis of fatty acids in the liver are corrected in animal experiments by the administration of lipoic acid (S. S. Wagh, C. V. Natraj et al., J. Biosci. vol. 11, 59–74 (1987)).

Transfer factor is produced by leucocytes and lymphocytes, and comprises small water soluble polypeptides of about eight amino acids and also associated cofactors that stimulate or transfer cell mediated immunity from one individual to another and across species. These immune system hormones may balance the immune system and prevent it from damaging tissues in diabetic patients. Since transfer factors are smaller than antibodies, they do not transfer antibody mediated responses nor do they induce antibody production. The properties, characteristics and processes for obtaining transfer factor or transfer factors are discussed in U.S. Pat. Nos. 4,816,563, 5,080,895, 5,840,700, 5,883,224 and 6,506,413.

Polymannose is a long chain essential saccharide known to stimulate the immune system and sold for example, as in a composition under the trade mark "Manapol" by Carrington Laboratories. Polymannose is a component of the herb aloe barbensis and glycosylates enzymes in the liver that are resonsibe for glucose production (gluconeogenesis), which can be abnormal in diabetes patients, thus lowering blood glucose levels and glucose production when the liver senses they are too high. Furthermore, the mannose can glycosylate cell mebrane glycoproteins important in insulin binding, leading to improved cellular response to insulin.

Fenugreek, a slender annual herb of the pea family, may decrease cortisol production in the body when it is too high, leading to lowered blood glucose levels and complications of elevated cortisol such as accelerated aging and heart disease. Its dried seeds have been used for generations as a food, a flavoring, and a medicine. Steroidal saponins may account for many of the beneficial effects of fenugreek, particularly the inhibition of cholesterol absorption and synthesis. The seeds are rich in dietary fiber. The use of fenugreek in a composition for treatment of diabetes is disclosed, for example, in U.S. Pat. No. 6,451,355 to Reisner.

Co-enzyme Q-10 (ubiquinone) is a dietary supplement used to treat a variety of problems. It is both an important antioxidant lowering oxidative stress and is also crucial for normal heart function. Levels are decreased in diabetes patients, and raising them may lower the risk of heart disease, which is the number one killer in diabetics, and also lowers glucose requirements in the heart, resulting in lower blood levels. U.S. Pat. No. 6,300,377 to Chopra discloses the use of a combination of ubiquinone and alpha lipoic acid for treatment of diabetes.

The remaining components of the composition are known dietary supplements.

Selenium is crucial for many cellular functions and is deficient in diabetics. Normalized levels may stimulate insulin production in type II diabetics, and also may prevent complications in other tissues.

Vitamin C is crucial for multiple processes in the human body. It tends to be deficient in diabetics and replacement appears to improve the active transport of glucose from the bloodstream across the cell membrane into cells.

Vitamin E is also deficient in diabetics. Restoring normal levels improves antioxidant function and also enhances glucose transport across the cell membrane by helping to normalize and upregulate insulin receptors.

Chromium is crucial in cell metabolism. Normalizing metabolism by restoring normal levels decreases the need for glucose in cells, feeding back a message to the pancreas to produce less insulin and the liver to produce less glucose.

Vanadium is a trace mineral which is low in almost all diabetics. It can lower blood sugar levels in all diabetics by enhancing glucose metabolism inside the cells.

Zinc is a mineral necessary for proper immune function, and is deficient in almost all diabetic patients, contributing to the complications.

Preferably, zinc is added as zinc glycinate, selenium as selenomethionine, chromium as chromium picolinate, vanadium as vanadyl sulfate and vitamin E as d-alpha-tocopherol succinate.

In a typical composition according to the invention, the components described above are ground and formed into a tablet, optionally with adjuvants as are known in the art. Each dose typically contains:

| | |
|---|---|
| Agaricus blazeii | 100 mg |
| alpha lipoic acid | 70 mg |
| transfer factor | 70 mg |
| polymannose | 100 mg |
| fenugreek | 20 mg |
| coenzyme Q-10 | 40 mg |
| selenium (as selenomethionine) | 50 µg |
| zinc (as zinc glycinate) | 1 mg |
| vitamin C (as ascorbic acid) | 25 mg |
| vitamin E (as d-α-tocopherol succinate) | 25 IU |
| chromium (as chromium picolinate) | 25 µg |
| vanadium (as vanadyl sulfate) | 10 µg |

EXAMPLES

Example 1

Confluent monolayers of murine islet, fat and hepatic cells were periodically stimulated to produce glucose into the supernatant by withholding Fetal Bovine Serum (FBS) in the presence of the typical inventive composition above, individual components added at 1 h intervals (50 µg/ml each) and no additive (negative control).

Results: supernatant blood sugar levels measured ½ h after sequentially adding each component (90 min after withholding FBS) resulted in supernatant glucose levels as follows:

| Glucose levels | (µg/dl) |
|---|---|
| No additive: | 113.8 |
| Combination | 19.3 |
| Individual | 49.7 |

$p<0.01$: there is less than 1 in 100 chance that the differences noted in the study are random rather than based on the results of the medications administered.

Use of the composition of the invention resulted in significantly lower glucose levels produced by islet cells as compared to the individual ingredients added sequentially. We attempted to duplicate real-life conditions by continuous levels in the supernatant, as may be expected by dosing all ingredients at the same time, versus adding the ingredients sequentially, as may be the situation when a patient attempts to take the ingredients throughout the day (which is the recommended method since taking such a large number of supplements simultaneously is not feasible from a gastrointestinal tolerability aspect). While not wishing to be held to any particular explanation, it is theorized that the combination of components work synergistically and simultaneously on hepatic, fat and islet cells to produce lowered glucose levels while individual components lack synergy when used sequentially.

Example 2

A 30 day study was conducted of 20 persons with type II DM according to the following protocol:

Patients with documented type II diabetes mellitus were eligible. They received the composition of the invention described above as the typical composition in tablet form 3 times per day, while reducing their normal diabetes medication as appropriate, based on their reduced blood sugar levels. Patients closely monitored their blood sugar by glucometer, fingerstick strips or urine, daily during the 30-day trial. A physician team carefully evaluated patients by lab values, physical exams and symptoms for any potential problems. Participants were monitored once per week, at which time a serum blood glucose, hemoglobin A1C, chemistry panel, CBC and urinalysis were obtained. A follow-up visit 1 month after the conclusion of the active phase of the study occurred.

The results of the study are set forth in the table below.

TABLE

| Patient No. | Medication | Starting Blood Sugar | Ending Blood Sugar | Reduction in Blood Sugar | Reduction in Medicine Taken- % |
|---|---|---|---|---|---|
| 1 | Insulin | 189 | 138 | 51 | 60 |
| 2 | Oral | 239 | 122 | 117 | 100 |
| 3 | Oral | 258 | 128 | 130 | 50 |
| 4 | Oral | 341 | 142 | 199 | 75 |
| 5 | Insulin | 165 | 104 | 61 | 0 |
| 6 | Oral | 246 | 138 | 108 | 50 |
| 7 | Oral | 154 | 98 | 56 | 100 |
| 8 | Insulin | 226 | 116 | 110 | 25 |
| 9 | Insulin | 198 | 119 | 79 | 40 |
| 10 | Oral | 268 | 143 | 125 | 100 |
| 11 | Insulin | 307 | 156 | 151 | 50 |
| 12 | Oral | 254 | 135 | 119 | 0 |
| 13 | Oral | 276 | 154 | 122 | 50 |
| 14 | Insulin | 165 | 116 | 49 | 25 |
| 15 | Insulin | 215 | 91 | 124 | 75 |
| 16 | Oral | 249 | 118 | 131 | 25 |
| 17 | Oral | 214 | 97 | 117 | 50 |
| 18 | Insulin | 175 | 105 | 70 | 0 |
| 19 | Insulin | 211 | 123 | 88 | 50 |
| 20 | Oral | 253 | 88 | 165 | 100 |
| Average | | 242.8 | 117.9 | 124.9 | |

Out of nine patients taking insulin, eight were able to reduce insulin usage, five by more than 50%. Out of eleven patients taking oral hypoglycemics, nine were able to reduce medication usage by more than 50%. The average fasting blood sugar for the patient group was reduced by more than 50%.

What is claimed is:

1. A composition for reducing blood sugar in humans in need thereof, comprising effective amounts of:

*Agaricus blazeii;*
alpha lipoic acid;
transfer factor;
polymannose;
fenugreek;
coenzyme Q-10;
selenium;
zinc;
vitamin C;
vitamin E;
chromium; and
vanadium.

2. A composition according to claim 1, comprising, in % by weight:

| *Agaricus blazeii* | 20–30; |
| alpha lipoic acid | 15–20; |
| transfer factor | 15–20; |
| polymannose | 20–30; |

-continued

| fenugreek | 4–6; |
| coenzyme Q-10 | 8–12; |
| selenium | 0.01–0.03; |
| zinc | 0.1–0.3; |
| vitamin C | 4–6; |
| vitamin E | 3–5; |
| chromium | 0.004–0.01; and |
| vanadium | 0.001–0.004. |

3. A composition according to claim 1 in the form of a tablet for a dosage unit comprising:

| *Agaricus blazeii* | 100 mg; |
| alpha lipoic acid | 70 mg; |
| transfer factor | 70 mg; |
| polymannose | 100 mg; |
| fenugreek | 20 mg; |
| coenzyme Q-10 | 40 mg; |
| selenomethionine to provide selenium in an amount of: | 50 µg; |
| zinc glycinate to provide zinc in an amount of: | 1 mg; |
| ascorbic acid to provide vitamin C in an amount of: | 25 mg; |
| d-α-tocopherol succinate to provide vitamin E in an amount of: | 25 IU; |
| chromium picolinate to provide chromium in an amount of: | 25 µg; and |
| vanadyl sulfate to provide vanadium in an amount of: | 10 µg. |

4. A method for treatment of diabetes, comprising administering to a person in need thereof a composition comprising effective amounts of:

*Agaricus blazeii;*
alpha lipoic acid;
transfer factor;
polymannose;
fenugreek;
coenzyme Q-10;
selenium;
zinc;
vitamin C;
vitamin E;
chromium; and
vanadium.

5. A method according to claim 4, wherein the composition comprises, in % by weight:

| *Agaricus blazeii* | 20–30; |
| alpha lipoic acid | 15–20; |
| transfer factor | 15–20; |
| polymannose | 20–30; |
| fenugreek | 4–6; |
| coenzyme Q-10 | 8–12; |
| selenium | 0.01–0.03; |
| zinc | 0.1–0.3; |
| vitamin C | 4–6; |
| vitamin E | 3–5; |
| chromium | 0.004–0.01; and |
| vanadium | 0.001–0.004. |

6. A method according to claim 4, wherein the composition is administered in the form of a tablet for a dosage unit comprising:

| | |
|---|---|
| *Agaricus blazeii* | 100 mg; |
| alpha lipoic acid | 70 mg; |
| transfer factor | 70 mg; |
| polymannose | 100 mg; |
| fenugreek | 20 mg; |
| coenzyme Q-10 | 40 mg; |
| selenomethionine to provide selenium in an amount of: | 50 µg; |
| zinc glycinate to provide zinc in an amount of: | 1 mg; |
| ascorbic acid to provide vitamin C in an amount of: | 25 mg; |

-continued

| | |
|---|---|
| d-α-tocopherol succinate to provide vitamin E in an amount of: | 25 IU; |
| chromium picolinate to provide chromium in an amount of: | 25 µg; and |
| vanadyl sulfate to provide vanadium in an amount of: | 10 µg. |

7. A method according to claim 6, wherein the tablet is administered three times per day.

* * * * *